United States Patent
Siino, Jr. et al.

(10) Patent No.: US 9,945,866 B2
(45) Date of Patent: Apr. 17, 2018

(54) PROTEIN STANDARD

(71) Applicant: Bio-Rad Laboratories, Inc., Hercules, CA (US)

(72) Inventors: Joseph S. Siino, Jr., Benicia, CA (US); Dennis C. Yee, Walnut Creek, CA (US); Robin Baginski, Vacaville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 785 days.

(21) Appl. No.: 14/209,185

(22) Filed: Mar. 13, 2014

(65) Prior Publication Data

US 2014/0311909 A1    Oct. 23, 2014

Related U.S. Application Data

(60) Provisional application No. 61/784,242, filed on Mar. 14, 2013.

(51) Int. Cl.
*G01N 27/447* (2006.01)
*G01N 33/68* (2006.01)

(52) U.S. Cl.
CPC ... *G01N 33/6803* (2013.01); *G01N 27/44726* (2013.01)

(58) Field of Classification Search
None
See application file for complete search history.

(56) References Cited

U.S. PATENT DOCUMENTS 4,375,972 A    3/1983    Forgione et al.
5,200,509 A *  4/1993    Spencer ............. C07K 14/4743
                                                530/350
(Continued)

FOREIGN PATENT DOCUMENTS

EP    0 437 920 A1    7/1991
GB    2272698 A       5/1994
(Continued)

OTHER PUBLICATIONS

"Protein Standards: Precision Plus Protein WesternC Standards—Versatile, Multi-Application Protein Standards: Colorimetric, Chemiluminescent, and Fluorescent Properties All in One," Datasheet [online]. Bio-Rad Laboratories, Inc., Dec. 20, 2012. [retrieved on Sep. 30, 2016]. Retrieved from the internet : <URL: http://www.bio-rad.com/webroot/web/pdf/lsr/literature/Bulletin_5661.pdf.>, 2 pages.

(Continued)

*Primary Examiner* — Jill A Warden
*Assistant Examiner* — Julie L Tavares
(74) *Attorney, Agent, or Firm* — Kilpatrick Townsend and Stockton LLP (57) ABSTRACT

Disclosed herein is a protein standard for gel electrophoresis. The standard may be detected using multiple modalities. These modalities include, for example, observation of color or fluorescence arising from dyes, porphyrins, or haloalkylated tryptophan residues covalently linked to proteins of the standard; or detection of fluorescence or chemiluminescence arising from antibodies or other binding partners bound to proteins of the standard through polypeptide epitopes or affinity tags. The protein standard comprises multiple protein sets, each set corresponding to a different gel band, and proteins within a set may be detectable with one or more modalities.

18 Claims, 2 Drawing Sheets

(56) References Cited

U.S. PATENT DOCUMENTS

| | | | |
|---|---|---|---|
| 5,506,121 | A | 4/1996 | Schmidt et al. |
| 6,130,101 | A | 10/2000 | Mao et al. |
| 6,841,359 | B2 | 1/2005 | Szostak et al. |
| 7,166,478 | B2 | 1/2007 | Stavrianopoulos et al. |
| 7,537,751 | B2 | 5/2009 | Stavrianopoulos et al. |
| 8,007,646 | B2 | 8/2011 | Edwards et al. |
| 8,012,715 | B2 | 9/2011 | Chatterjee et al. |
| 8,076,452 | B2 | 12/2011 | Lamla et al. |
| 2002/0177196 | A1 | 11/2002 | Maier et al. |
| 2003/0148532 | A1 | 8/2003 | Edwards et al. |
| 2004/0014071 | A1* | 1/2004 | Rothschild ............. C12P 19/34 435/6.13 |
| 2010/0089753 | A1* | 4/2010 | Edwards ............ G01N 33/6827 204/461 |
| 2013/0266579 | A1* | 10/2013 | Wei ................... C07K 16/2863 424/158.1 |
| 2013/0288388 | A1 | 10/2013 | Freeby et al. |

FOREIGN PATENT DOCUMENTS

| | | |
|---|---|---|
| WO | 2011/031497 A2 | 3/2011 |
| WO | 2014/004959 A1 | 1/2014 |

OTHER PUBLICATIONS

Korndorfer, Ingo P., et al., "Improved affinity of engineered streptavidin for the Strep-tag II peptide is due to a fixed open conformation of the lid-like loop at the binding site," Apr. 1, 2001, Protein Science, vol. 11, No. 4, pp. 883-893.

Urban, Michael, et al., "Moledular Weight Estimation and Quantitation of Protein Samples Using Precision Plus Protein WesternC Standards, the Immun-Star WesternC Chemiluminescence Detection Kit, and the ChemiDoc XRS Imaging System," [online]. Bio-Rad Laboratories, Inc., Mar. 28, 2011. [retrieved on Sep. 30, 2016]. Retrieved from the internet : <URL: http://www.bio-rad.com/webroot/web/pdf/lsrt/literature/Bulletin_5576.pdf.>, 6 pages.

Supplementary Partial European Search Report dated Oct. 19, 2016 in EP 14775598.7, 8 pages.

GenBank (GenPept) Accession No. XP_001727767, dated Jun. 3, 2004. 1,3-beta-glucanosyltransferase [*Aspergillus oryzae* RIB40]. Sawano et al.

Della-Penna et al.; "Biotinylated Proteins as Molecular Weight Standards on Western Blots"; *Analytical Biochemistry*; 152(2):329-332 (1986).

Kazmin et al.; "Visualization of proteins in acrylamide gels using ultraviolet illumination"; *Analytical Biochemistry*; 301:91-96 (2002).

Maurizi et al.; "Peroxidase-active molecular weight markers for direct detection in western blot"; *Analytical Biochemistry*; 286:295-296 (2000).

Pikuleva et al.; "A new method of preparing hemin conjugate with rabbit IgG"; Bioorg Khim.; 11:1480-1483 (1989).

Pinchuk et al.; "Spectral characteristics and mechanisms of forming "chloroform-dependent" tryptophan photoproducts"; *J. Appl. Spectrosc.*; 59:711-715 (1993).

Privat et al.; "Photochemical modifications of the tryptophan residues of wheat-germ agglutinin in the presence of trichloroethanol"; *Eur. J. Biochem.*; 84(1):79-85 (1978).

Schmidt et al.; "Molecular Interaction Between the Strep-tag Affinity Peptide and its Cognate Target, Streptavidin"; *J. Mol. Biol.*; 255:753-766 (1996).

Voropei et al.; "Chloroform-dependent photoproducts of tryptophan"; *Biophysics*; 37(5):743-745—(1992).

Author unknown. Chemiluminescent BlueRanger™ Prestained Peroxidase-Labeled Protein Molecular Weight Marker. (#26651, Instructions) Pierce Biotechnology, Inc. (Oct. 2006).

Author unknown. PageRuler™ Plus Prestained Protein Ladder. (#26619, Instructions). Thermo Scientific (2010).

Author unknown. PageRuler™ Prestained NIR Protein Ladder. (#26635, Instructions). Thermo Scientific (2011).

Author unknown. Spectra™ Multicolor Broad Range Protein Ladder. (#26634, Instructions). Thermo Scientific (2012).

International Search Report and Written Opinion from International Application No. PCT/US2014/026204, dated Oct. 8, 2014.

Extended European Search Report from EP Appln No. 14775598.7, 13 pages, dated Jan. 20, 2017.

* cited by examiner

FIG. 1

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: synthetic affinity tag STP1, recognition
      sequence, antibody-binding epitope

<400> SEQUENCE: 1

Trp Thr His Pro Gln Phe Glu Arg
 1               5

<210> SEQ ID NO 2
<211> LENGTH: 9
<212> TYPE: PRT
<213> ORGANISM: Artificial Sequence
<220> FEATURE:
<223> OTHER INFORMATION: synthetic affinity tag Strep-TagI, recognition
      sequence, antibody-binding epitope

<400> SEQUENCE: 2

Ala Trp Arg His Pro Gln Phe Gly Gly
 1               5

<210> SEQ ID NO 3
<211> LENGTH: 8
<212> TYPE: PRT
<213> ORGANISM: Artificial Sequence
<220> FEATURE:
<223> OTHER INFORMATION: synthetic affinity tag Strep-TagII, recognition
      sequence, antibody-binding epitope

<400> SEQUENCE: 3

Trp Ser His Pro Gln Phe Glu Lys
 1               5
```

PROTEIN STANDARD

CROSS-REFERENCES TO RELATED APPLICATIONS

The present application claims priority to U.S. Provisional Patent Application No. 61/784,242, entitled "PROTEIN STANDARD" and filed Mar. 14, 2013, which is incorporated herein by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 94263-902518.TXT, created on May 19, 2014, 4,096 byte, machine format IBM-PC, MS-Windows operating system, is hereby incorporated by reference in its entirety for all purposes.

BACKGROUND OF THE INVENTION

Protein gel electrophoresis is a ubiquitous technique in molecular biology research, pharmaceutical manufacturing, and other enterprises. The technique may be used to analyze the protein content of a biological sample or purify sufficient quantities of a protein of interest for later use. An essential aspect of protein gel electrophoresis is detection of sample proteins in the gel, which allows characterization of these proteins in terms of molecular weight, purity, amino acid content, etc. To aid such characterization, skilled practitioners often make use of a protein standard—a group of well-characterized proteins that is run in the gel alongside the sample proteins.

New technologies have made the detection of proteins following electrophoresis more sensitive, more specific, and less costly. Many of these technologies require that the proteins to be detected have particular features, such as specific amino acid motifs or covalently attached chemical groups.

BRIEF SUMMARY OF THE INVENTION

Provided herein are protein standards, methods of detecting protein standards, and kits for detecting protein standards.

A protein standards for gel electrophoresis is provided. In some embodiments, the standard includes multiple protein sets, each set corresponding to a different gel band, wherein at least one set comprises a labeled protein comprising (i) a tryptophan residue and (ii) a label, said label being spectrally distinct from haloalkylated tryptophan. In other embodiments, the standard includes multiple protein sets, each set corresponding to a different gel band, wherein at least one set comprises a mixture of unlabeled and labeled proteins, said unlabeled protein comprising a tryptophan residue, and said labeled protein comprising a label that is spectrally distinct from haloalkylated tryptophan.

The tryptophan residue may be covalently linked to a haloalkane. The haloalkane may have one or two carbon atoms, or may be selected from the group including but not limited to trichloroethanol, trichloroacetic acid, chloroform, and bromoform.

In some embodiments of the protein standard, the label of the labeled protein is an amino acid residue covalently linked to a porphyrin. In other embodiments, the label is an amino acid residue covalently linked to a dye.

The dye may be selected from the group consisting of Uniblue A, Neutral Red, QXL610, QXL670, Yellow RGA, DEAC, NBD-X, Bodipy TMR-X, Bodipy TR-X, Bodipy 530, Bodipy R6G, Bodipy 493, Dansyl-X, hemin, and protoporphyrin IX. The dye may be colored or fluorescent. In some cases, the dye is fluorescent and the peaks of the excitation and emission spectra of the dye fall in the visible spectrum.

In some embodiments of the protein standard, 2, 3, 4, 5, 6, 7, 8, 9, 10, 11, or 12 protein sets of the standard comprise a mixture as recited above. In other embodiments, all protein sets of the standard comprise such a mixture. In still other embodiments, 2, 3, 4, 5, 6, 7, 8, 9, 10, 11, or 12 protein sets of the standard comprise a protein comprising a tryptophan residue, as recited above. In additional embodiments, all protein sets of the standard comprise a protein comprising such a tryptophan residue. In yet other embodiments, 2, 3, 4, 5, 6, 7, 8, 9, 10, 11, or 12 protein sets of the standard comprise a protein comprising a label, as recited above. In still other embodiments, all protein sets of the standard comprise a protein comprising such a label.

The label of a protein of a first protein set may be spectrally distinct from the label of a protein of a second protein set. The labeled protein of the at least one set may also comprise, on average, fewer than 2, 5, 10, or 20 such labels per molecule. Alternatively, the labeled protein of the at least one set may comprise, on average, more than 2, 5, 10, or 20 such labels per molecule.

In some embodiments of the protein standard, wherein at least one protein set comprises a mixture of unlabeled and labeled protein, the ratio of labeled to unlabeled protein molecules in the at least one set is at most 1:10, 1:5, 1:2, 1:1, 2:1, 5:1, or 10:1. In other such embodiments, the average molecular weight of the labeled protein in the at least one set exceeds that of the unlabeled protein in the same set by at least 1%, 2%, 5%, 10%, or 20%.

The protein sets of the standard may correspond to molecular weights in the range 10 to 250 kDa, or differ in molecular weight by at least 1, 2, 5, 10, 20, 50, or 100 kDa. In some embodiments of the protein standard, the label of the labeled protein is stable in the presence of reducing agents. In other embodiments, the at least one set further comprises an additional labeled protein, and the label of the labeled protein is spectrally distinct from the label of the additional labeled protein.

In the provided protein standards, the labeled protein of the at least one set may further comprise a detectable moiety. The moiety may be a dye, porphyrin, or polypeptide, for example. In some embodiments, wherein the moiety is a polypeptide, the polypeptide occurs at the N- or C-terminus of the labeled protein. In other such embodiments, the polypeptide is covalently linked to an amino acid side-chain of the labeled protein. In still other such embodiments, the polypeptide is a recognition sequence.

In some cases, the recognition sequence is an antibody-binding epitope. In other cases, the recognition sequence is an affinity tag. The affinity may be a Strep-tag or comprise the amino acid sequence WTHPQFER (SEQ ID NO: 1), for example.

In some embodiments, a protein standard includes multiple protein sets, each set corresponding to a different gel band, wherein at least one set comprises a protein comprising the amino acid sequence WTHPQFER (SEQ ID NO: 1), AWRHPQFGG (SEQ ID NO: 2), or WSHPQFEK (SEQ ID NO: 3). In other embodiments, the standard includes multiple protein sets, each set corresponding to a different gel band, wherein at least one set comprises a protein comprising an amino acid sequence which has binding affinity for streptavidin or Strep-Tactin. In some of these embodiments, the protein of the at least one set further comprises a label, said label comprising an amino acid residue covalently linked to a dye. Further, in some cases, the amino acid residue of the label is not within said amino acid sequence.

In some embodiments, the standard includes multiple protein sets, each set corresponding to a different gel band, wherein at least one set comprises a mixture of a first labeled protein and a second labeled protein, said first labeled protein comprising a first label and said second labeled protein comprising a second label, and wherein the first and second labels are spectrally distinct.

A method of detecting a protein standard after gel electrophoresis is also provided. In some embodiments, the method includes providing an electrophoresis gel comprising a protein standard as recited above, and optically detecting the standard. The protein standard may occur in the gel at a concentration of at least 0.5, 1, 2, 5, 10, 20, 30, or 40 micrograms total protein per lane, for example. The protein standard comprises multiple protein sets, each set corresponding to a different gel band, and at least one protein set may occur in the gel at a concentration of at least 0.1, 0.2, 0.5, 1, 2, 5, or 10 micrograms per lane.

In some embodiments, the method further comprises illuminating the gel with UV light and detecting the fluorescence of any haloalkylated tryptophan residues in the standard. The UV light may have a wavelength of 250-340 nm, for example. The gel may further comprise a haloalkane, which in some cases may be selected from the group including but not limited to trichloroethanol, trichloroacetic acid, chloroform, and bromoform.

The optical detection of the method may comprise illuminating the gel with ambient light or visible light. Such visible light may have a wavelength of 400-700 nm, for example.

In some embodiments of the method, the optical detection comprises visualizing color arising from the label of the labeled protein. In other embodiments, the optical detection comprises detecting the absorption or fluorescent re-emission of visible light by the label of the labeled protein. In still other embodiments, the method further comprises transferring the labeled protein from the gel to a blotting membrane, and detecting the labeled protein on the membrane.

Such detection of the labeled protein on the membrane may comprise: providing a binding partner specific for the label or moiety of the labeled protein; incubating the membrane with the binding partner; and, detecting the interaction of the binding partner with the labeled protein on the membrane. The binding partner may be a protein, and in some cases an antibody. The interaction of the binding partner with the labeled protein may be detected by fluorescence or chemiluminescence, for example.

In some embodiments, wherein the method comprises detecting the labeled protein on a membrane, the label or moiety is protoporphyrin IX. The binding partner may be luminol, and interaction of the binding partner with the labeled protein may be detected by chemiluminescence.

In other embodiments, wherein the method comprises detecting the labeled protein on a membrane, the moiety is selected from the group consisting of Strep-TagI, Strep-TagII, or STP1. The binding partner may comprise streptavidin or Strep-Tactin, and interaction of the binding partner with the labeled protein may be detected by fluorescence or chemiluminescence.

In some embodiments, the method includes: providing a protein standard, the standard comprising multiple protein sets, each set corresponding to a different gel band, wherein at least one set comprises a labeled protein comprising: a label comprising an amino acid residue covalently linked to a dye, and the amino acid sequence WTHPQFER (SEQ ID NO: 1), AWRHPQFGG (SEQ ID NO: 2), or WSHPQFEK (SEQ ID NO: 3); illuminating a gel containing the protein standard with visible light; detecting the absorption or fluorescent re-emission of said visible light by the label; transferring the labeled protein to a blotting membrane; incubating the membrane with a binding partner specific for said amino acid sequence; and, detecting the binding partner bound to the labeled protein on the membrane.

In some embodiments of this method, the at least one set further comprises an unlabeled protein comprising a tryptophan residue, the gel further comprises a haloalkane, and the method further comprises: illuminating the gel with UV light, whereupon the tryptophan residue of the unlabeled protein reacts with the haloalkane to form a covalent adduct; and detecting light resulting from fluorescence of said covalent adduct. In other embodiments of this method, the labeled protein further comprises a tryptophan residue, the gel further comprises a haloalkane, and the method further comprises: illuminating the gel with UV light, whereupon the tryptophan residue of the labeled protein reacts with the haloalkane to form a covalent adduct; and, detecting light resulting from fluorescence of said covalent adduct. The amino acid residue of the label may be a lysine residue, for example. The binding partner may comprise streptavidin or Strep-Tactin.

A kit for detecting a protein standard in a gel is also provided. In some embodiments, the kit includes a protein standard as recited above, and a haloalkane. The kit may further comprise a gel, wherein the haloalkane is a component of the gel. In some embodiments of the kit, a labeled protein of the standard comprises a moiety detectable on a blotting membrane, and the kit further comprises a binding partner specific for said moiety for use in such detection.

BRIEF DESCRIPTION OF THE DRAWINGS

FIGS. 2A, 2B, and 2C show detection of five protein standards using three detection modalities, as discussed in Example 2.

DETAILED DESCRIPTION OF THE INVENTION

Provided herein is a protein standard for gel electrophoresis that can be detected using one or more detection modalities. In general, a protein standard is a group of proteins that are well characterized in terms of molecular weight, size, or other qualities. The standard is typically run on an electrophoresis gel along with a sample protein or proteins of interest. By detecting the standard and sample proteins, one can compare characteristics of the standard and sample proteins and thereby experimentally characterize the sample protein(s). The multiple detection modalities discussed herein allow the sample protein(s) to be characterized in multiple ways.

The protein standard described herein comprises multiple (e.g. 2, 3, 4, 5, 6, 7, 8, 9, 10, 11, 12, or more) protein sets, where proteins within one set migrate together on an electrophoresis gel. The proteins within a set typically have similar molecular weights and/or sizes. After the gel has been loaded and run for sufficient time, the proteins in the set will appear together on the gel, thereby constituting a 'band' on the gel, using one or more detection modalities. As used herein, a 'protein set' corresponds to the proteins found in one gel band, where the gel is prepared and run using standard methods (see, for example, Sambrook and Russell, *Molecular Cloning: A Laboratory Manual* (3rd ed.), New York: Cold Spring Harbor Laboratory Press, 2001). Different protein sets correspond to different gel bands.

A gel band has finite width in the direction of protein migration, and in some cases more than one maximum in density, as a result of heterogeneity in the molecular weights and/or sizes of proteins in the corresponding protein set, or as a result of the limited capacity of the gel to accommodate proteins. If a protein set is detected using more than one modality, then the modalities will tend to report similar shapes, density profiles, locations, and other characteristics for the associated gel band, and any disagreement between the modalities may reflect heterogeneity of proteins in the set. A band that appears in two locations (i.e. has two maxima in density), as detected using one modality or different modalities, is said to be 'bifurcated' or a 'doublet'.

In one aspect of the standard, at least one protein set (e.g. 1, 2, 3, 4, 5, 6, 7, 8, 9, 10, 11, 12, or more protein sets, or all protein sets of the standard) comprises a protein having a tryptophan residue. Tryptophan, one of the twenty standard amino acids, can be reacted with a haloalkane to form a detectable fluorescent product. The reaction has been described previously (see, for example, U.S. Pat. No. 8,007,646; Edwards et al., *Photochem. & Photobiol.* 75, 362-368, 2002; Kazmin et al., *Anal. Biochem.* 301, 91-96, 2002) and involves the UV-induced addition of the haloalkane to the indole side-chain. In some embodiments, the haloalkane reactant has one or two carbon atoms. Examples of suitable haloalkane reactants include, without limitation, trichloroethanol, trichloroacetic acid, chloroform, and bromoform. Although the halogen atoms of the haloalkane can dissociate from the tryptophan side-chain as the reaction is resolved, the tryptophan remains covalently linked to carbon, oxygen, and/or hydrogen atoms of the haloalkane as a result of the reaction, and is said herein to be 'haloalkylated'. The reaction may be performed before or after the protein standard has been loaded and run on an electrophoresis gel. In the latter case, the haloalkane may be a component of the gel, and the reaction can be carried out in situ, by exposing the gel to UV light.

Once haloalkylated, tryptophan fluoresces upon further exposure to UV light. Haloalkylated tryptophan adducts have excitation maxima in the range ~300-400 nm and emission maxima in the range ~400-500 nm. The same UV light, such as that available from a UV transilluminator (~250-340 nm), can be used to catalyze the haloalkylation reaction and induce fluorescence. Suitable detection optics for visible light may be used in combination with a UV transilluminator to detect haloalkylated standard and sample proteins in an electrophoresis gel after the gel has been run. The haloalkylation reaction, and the associated reagents, apparatus, and methods used to perform the reaction and detect products thereof, are sometimes referred to by the name 'Stain-Free™' (Bio-Rad). It will be recognized that a protein compatible with Stain-Free detection does not need to have a tryptophan residue available for haloakylation, but instead can be linked to a fluorescent dye with similar excitation and emission properties as haloalkylated tryptophan. A protein linked to such a dye can be detected upon UV illumination, under the same or similar conditions used to detect haloalkylated tryptophan.

At least one protein set (e.g. 1, 2, 3, 4, 5, 6, 7, 8, 9, 10, 11, 12, or more protein sets, or all protein sets) of the standard described herein may further comprise a labeled protein, i.e., a protein having a label. The label can be on the same protein molecule as the tryptophan residue subject to haloalkylation, or a different molecule, as is discussed below. In some embodiments, the label is detected optically, such as by eye or with fluorescence, among other available methods. In some embodiments, the label is spectrally distinct from haloalkylated tryptophan. Herein, two species are considered 'spectrally distinct' if they absorb or emit light at different maximum (i.e. peak) wavelengths, have nonoverlapping absorption, excitation, or emission spectra, or have otherwise sufficiently different optical properties that one species may be detected without preventing or interfering with detection of the other species.

In some embodiments, the label is a porphyrin molecule. Porphyrins, described for example in Ogoshi & Mizutani, *Curr. Opin. Chem. Biol.* 3, 736-739, 1999, are organic heterocyclic macrocycles that can coordinate metal ions in the center of the ring structure. Examples of porphyrins include porphine, protoporphyrin IX, and hemin (an iron-bound form of protoporphyrin IX). Porphyrins containing a free carboxyl group can be activated using TSTU (O—(N-succinimidyl)-N,N,N',N'-tetramethyluronium tetrafluoroborate) to generate amino reactive succinimidyl esters, which react selectively with primary amines on protein molecules. Protoporphyrin IX has fluorescence excitation and emission maxima at 402 and 633 nm, respectively. When linked to a protein, protoporphyin IX was found to exhibit fluorescence detectable upon excitation with a UV transilluminator and also upon visible excitation at both 530 nm and 630 nm. Porphyrins with broad excitation spectra are compatible with multiple illumination and detection methods and apparatus.

In other embodiments, the label is a dye. Without limiting the generality of the term, a dye is typically an aromatic organic molecule that absorbs visible light and exhibits color and/or fluorescence. An example of a dye used for labeling proteins of the standards described herein is Uniblue A (1-amino-9,10-dihydro-9,10-dioxo-4-[m-(vinylsulphonyl) anilino]anthracene-2-sulphonate), which absorbs at the red end of the visible spectrum, exhibits red fluorescent emission, and imparts a blue color to proteins to which it is bound. Another example is QXL610, which has similar spectral properties. Other non-limiting examples of dyes that may be used herein are diethylaminocoumarin (DEAC), Neutral Red (3-amino-7-dimethylamino-2-methylphenazine hydrochloride), QXL670, Yellow RGA, Dansyl-X (6-((5-dimethylaminonaphthalene-1-sulfonyl)amino) hexanoic acid), Bodipy TMR-X (6-((4,4-difluoro-1,3-dimethyl-5-(4-methoxyphenyl)-4-bora-3a,4a-diaza-s-indacene-2-propionyl)amino)hexanoic acid), Bodipy TR-X (6-(((4-(4,4-difluoro-5-(2-thienyl)-4-bora-3a,4a-diaza-s-indacene-3-yl) phenoxy)acetyl)amino)hexanoic acid), Bodipy 530 (4,4-difluoro-5,7-diphenyl-4-bora-3a,4a-diaza-s-indacene-3-propionic acid), Bodipy R6G (4,4-difluoro-5-phenyl-4-bora-3a,4a-diaza-s-indacene-3-propionic acid), Bodipy 493 (4,4-difluoro-1,3,5,7,8-pentamethyl-4-bora-3a,4a-diaza-s-indacene), ORCOReactive Brilliant Red RF3B (5-(benzoylamino)-4-hydroxy-3-[2-[1-sulfo-6-[[2-(sulfooxy)ethyl]sulfonyl]-2-naphthalenyl]diazenyl]-2,7-naphthalenedisulfonic acid), TRITC (5(6)-tetramethylrhodamine isothiocyanate), and NBD-X (6-(N-(7-nitrobenz-2-oxa-1,3-diazol-4-yl) amino)hexanoic acid).

Covalently linking a dye to a protein is sometimes called 'staining' Some dyes such as Neutral Red are not directly protein reactive but contain primary amines that can be linked to activating groups. Similarly, hetero-substituted phenazine and anthracene dyes and other dyes can be activated for protein labeling through primary amine, carboxylic acid or alcohol groups. For instance, trichlorotriazine (cyanuric acid) can react with free amines on heterocycles to form di- and mono-chlorotriazine linked dyes, which are reactive with protein amines. 1-Ethyl-3-(3-dimethylaminopropyl) carbodiimide (EDC) or N,N'-dicyclohexylcarbodiimide (DCC) can be used to activate carboxyl groups of dyes for reaction with protein primary amines (and alcohols when in the presence of DMAP; 4-dimethylaminopyridine). The activated dye can be reacted directly with the protein, or first with N-hydroxysuccinimide (NHS) or N-hydroxysulfosuccinimide (Sulfo-NHS) to form a succinimidyl ester, which can be isolated and subsequently reacted with the protein under mild conditions. Many protein-staining dyes, labeling chemistries, and labeling strategies are known in the art (see, for example, Johnson and Spence (Eds.), *Molecular Probes Handbook—A Guide to Fluorescent Probes and Labeling Technologies* (11th ed.), Eugene, Oreg.: 2010).

In some embodiments, the chemistry used to label a protein is chosen such that the label is stable in the presence of reducing agents such as dithiothreitol (DTT) or 2-mercaptoethanol. 'Stable' means that the label does not dissociate from the protein or undergo a chemical reaction that compromises its spectral properties. Reducing agents may be present in the buffers used to store the protein standards described herein.

A protein molecule may have multiple sites, such as lysine and cysteine side chains, that can react in one of the labeling reactions mentioned above, or in other labeling reactions known in the art. Accordingly, the parameters of the reaction may be adjusted to control the number of labels that become covalently linked to each protein molecule. These parameters include, for example, the stoichiometry of protein and label in the reaction and the temperature and duration of the reaction. A skilled artisan will recognize that the number of labels associated with each protein molecule after the labeling reaction is not uniform but rather follows a statistical distribution, and adjustment of reaction parameters may change the mean value or shape of the distribution. The distribution may be further affected by any purification procedures carried out after the reaction.

By controlling the number of labels per protein molecule, the makeup of the at least one protein set in the standard can be engineered to optimize detection using different optical modalities. The inventors surprisingly discovered that UV fluorescence from haloalkylated proteins is difficult to detect when these proteins are linked to brightly colored dyes and fluorescent dyes with high quantum yields, even when such dyes are spectrally distinct from haloalkylated tryptophan. The difficulty arises from the difference in magnitude of optical signals from the dyes and haloalkylated tryptophan. One solution is to detect proteins of the standard using dyes in lieu of, or in addition to, haloalkylated tryptophan upon UV illumination. For example, a fluorescent dye excitable by UV light, as well as a second dye excitable by visible light, can be linked to proteins in one protein set, either to the same molecules or to different molecules. Alternatively, to mitigate the difference in emission magnitudes between dye labels and haloalkylated tryptophan, the stoichiometry of labeling can be reduced, or labeled and unlabeled proteins can be mixed. (As the term is used herein, an 'unlabeled protein' may comprise a tryptophan residue available for haloalkylation or already haloalkylated). Accordingly, in some embodiments the concentrations of label and protein in the labeling reaction are chosen such that the resulting labeled protein has, on average, fewer than 2, 5, 10, or 20 labels per molecule. In other embodiments, labeled and unlabeled proteins are mixed at a ratio of at most 1:10, 1:5, 1:2, 1:1, 2:1, 5:1, or 10:1.

Due to the statistical nature of protein labeling reactions, a fraction of the protein molecules in a reaction generally remains unlabeled, and this fraction is significant at low labeling stoichiometries. A mixture of labeled and unlabeled proteins may therefore be the direct outcome of a labeling reaction, or the result of expressly mixing proteins isolated from a labeling reaction with proteins not subjected to such a reaction. (As used herein, 'express mixing' and grammatical equivalents thereof mean mixing together two or more molecular populations, or the solutions containing them, from separate containers.) In a protein set prepared as an express mixture, the ratio of labeled to unlabeled protein can be adjusted independently of the stoichiometry of labeling to achieve the desired abundances of tryptophan residues and labels. For example, as an alternative to labeling the protein at low stoichiometry, the protein can be labeled at high stoichiometry and then mixed with an unlabeled population. Accordingly, in some embodiments of the invention, the labeled protein has more than 2, 5, 10, or 20 labels per molecule.

Expressly mixing labeled and unlabeled protein in one protein set allows the label and haloalkylated tryptophan to occur on separate molecules. This has several advantages. First, it prevents interference between the two chemical groups, such as fluorescence resonance energy transfer or quenching, that may result from physical proximity and inhibit optical detection of one or both groups. Second, placing the two groups on separate molecules provides more options for the labeling reaction. For example, a labeling chemistry can be used wherein the label becomes covalently attached to tryptophan residues. Such a chemistry prevents the haloalkylation and detection of tryptophan residues on the labeled protein, but does not affect tryptophan residues on an unlabeled protein mixed into the same set after the reaction. Similarly, a labeling chemistry incompatible with tryptophan can be used by mixing a labeled tryptophan-free protein with an unlabeled protein containing tryptophan.

Mixing labeled and unlabeled protein also causes heterogeneity in the molecular weights of proteins of the protein set. Such heterogeneity may make the band associated with the set appear bifurcated when detecting the haloalkylated tryptophan and label. In this case, bifurcation is advantageous because it represents greater physical separation on the gel between protein molecules within the set (i.e., molecules bearing haloalkylated tryptophan and those bearing the label), further reducing any proximity-based interference. In some embodiments of the protein standard, the average molecular weight of labeled proteins in one protein set exceeds, or is greater than, that of unlabeled proteins in the same set by at least 1%, 2%, 5%, 10%, or 20% of the average molecular weight of unlabeled proteins in the set.

Regardless of how the protein set is prepared, in some embodiments the set comprises more than one labeled protein. For example, the set may comprise a protein labeled with a first label and the same protein (or a similar protein) labeled with a second label, wherein the first and second labels have different chemical compositions. Mixing proteins that are labeled differently allows more robust detection with multiple modalities. For example, one label may be strongly colored but weakly fluorescent; the other label may be strongly fluorescent but weakly colored. The mixture allows robust detection of both color and fluorescence. This is the case when the labels are, for example, the dyes Uniblue A and NBD-X. In some embodiments, the first and second labels are spectrally distinct. In such embodiments, one label may not be spectrally distinct from haloalkylated tryptophan, but may be detected in lieu of, or in addition to, haloalkylated tryptophan upon exposure to UV light.

A labeled protein of the at least one protein set may further comprise a detectable moiety. The moiety may be a porphyrin or dye, in addition to the porphyrin or dye that may comprise the label, as discussed above. Without limitation, such a moiety may be covalently attached to an amino acid side-chain of the labeled protein, or to the N- or C-terminus of the labeled protein. Methods for attaching more than one detectable chemical group (as distinct from multiple copies of the same group) are known in the art, and are reviewed in, for example, Johnson and Spence (Eds.), *Molecular Probes Handbook—A Guide to Fluorescent Probes and Labeling Technologies* (11th ed.), Eugene, Oreg.: 2010. Attaching multiple dyes to the same protein is often called 'containing' Costaining may be achieved by, among other methods, reacting dyes with a protein under different conditions. For example, Dansyl-X succinmidyl ester reacts optimally with appropriate amino acid side-chains at 25-37° C. and pH 7.5-8.5, while the vinyl sulfone group of Uniblue A reacts optimally at 60° C. and pH 9-10. By changing the temperature and pH, the reactions can be performed in succession.

Alternatively, the detectable moiety may be a polypeptide. Such a polypeptide may be part of a polypeptide chain of the labeled protein. Using standard molecular cloning techniques, a polypeptide sequence can be introduced into an existing protein, at the N- or C-terminus or elsewhere in the polypeptide chain. These techniques are reviewed in Sambrook and Russell, *Molecular Cloning: A Laboratory Manual* (3rd ed.), New York: Cold Spring Harbor Laboratory Press, 2001 and elsewhere. The polypeptide can also be chemically synthesized and attached to a protein through a chemical crosslinker. For example, the peptide may be activated at the N-terminus with EMCS (6-maleimidocaproic acid N-succinimidyl ester), making it reactive with free cysteine residues.

In some embodiments, the polypeptide may comprise an amino acid sequence that can be recognized with high affinity and specificity by a binding partner. Such a sequence is called a recognition sequence herein. Polypeptide moieties comprising a recognition sequence can be detected, for example, using electroblotting. As is well known in the art, electroblotting involves the transfer of proteins out of an electrophoresis gel after the gel has been run, using an electric field orthogonal to that used to run the gel. The transferred proteins are deposited onto the surface of a membrane (also called a 'blot' or 'blotting membrane'; typically made of nitrocellulose or polyvinylidene fluoride (PVDF)), which is then incubated in a solution containing the binding partner. Binding between the moiety and binding partner may be detected optically, for example using fluorescence or chemiluminescence, with radioactivity, or with other means known in the art.

If a recognition sequence takes an antibody as its binding partner, then the recognition sequence is termed an antibody-binding epitope or simply an epitope. Examples of epitopes commonly used in biotechnology are the FLAG and myc epitopes. A protein deposited on a blot can be detected using an antibody directed to an epitope of the protein, in a well-known technique called Western blotting. Detection can be accomplished, for example, by conjugating a fluorescent label to the antibody, illuminating the blot with an appropriate wavelength of light, and observing light re-emitted by the label. In place of the label, an appropriate enzymatic or chemical structure may be conjugated to the antibody to induce chemiluminescence. An example of such a structure is horseradish peroxidase (HRP), which catalyzes the oxidation of luminol to 3-aminophthalate in the presence of hydrogen peroxide and thereby causes visible light to be emitted. The antibody may alternatively incorporate a radioactive isotope such as $^{35}S$ and be detected using a Geiger counter or photographic film sensitive to decay of the isotope.

Instead of directly detecting the antibody that binds the epitope, a secondary antibody can be used. The secondary antibody has specificity for the epitope-binding antibody (known in the art as the 'primary antibody') and can be conjugated to a fluorescent label, catalyst of chemiluminescence, or other means of detection, as described above. Following incubation of the blot with the primary antibody, the blot may be incubated with the secondary antibody, and 'sandwiched' complexes comprising the secondary antibody bound to the primary antibody bound to the epitope may be detected. Under some conditions, the blot may be stripped of bound antibodies to allow detection of proteins on the blot using a different set of antibodies.

The recognition sequence instead may bind a protein that is not an antibody, or it may bind a small molecule. In this case, the recognition sequence may be referred to as an affinity tag (although the terms 'epitope' and 'affinity tag' are sometimes used interchangeably in the art). Examples of affinity tags are STP1 (amino acid sequence WTHPQFER, SEQ ID NO: 1), Strep-TagI (amino acid sequence AWRHPQFGG, SEQ ID NO: 2), and Strep-TagII (amino acid sequence WSHPQFEK, SEQ ID NO: 3) (collectively, 'Strep-tags'), which bind the protein streptavidin and an engineered mutant thereof called Strep-Tactin (see, for example, Schmidt et al., *J. Mol. Biol.* 255, 753-766, 1996). The STP1 tag lacks lysine or cysteine residues, which are often used as attachment sites for dyes in labeling proteins. Accordingly, the tag does not undergo covalent modification during many dye-labeling reactions and retains its affinity for its binding partner. The STP1 tag is therefore useful for detecting dye-labeled proteins on a blot following electroblotting. Like antibodies (discussed above), the binding partners of affinity tags may be conjugated to appropriate molecular means of detection.

Also provided herein are protein standards wherein at least one protein comprises a Strep-tag such as STP 1. The protein can, but need not, include a covalently linked dye or other label, as set forth above. Such embodiments are useful when optical detection of proteins in an electrophoresis gel is not needed, but detection on a blot is desired. The absence of a label in at least one protein set of the standard simplifies preparation of the standard and may reduce heterogeneity in the molecular weights of proteins in the set. This allows the molecular weights of sample proteins also comprising a Strep-tag to be estimated on the blot with greater precision.

In embodiments of the invention comprising a labeled protein, wherein the label or moiety is a porphyrin, the porphyrin may be detected as desired, including but not limited to by chemiluminescence following electroblotting. As discussed above, metal ions may be coordinated at the center of porphyrin ring structures. Metal ions, such as iron, catalyze luminol oxidation, and do so when bound to porphyrins. The inventors found that a protein labeled with hemin (iron-bound protoporphyrin IX) could be detected on a blot upon exposure of the blot to luminol and hydrogen peroxide.

The protein sets of the standard can be prepared individually and independently, and then combined. Accordingly, the number of protein sets comprising any particular element discussed herein, such as a tryptophan residue, a label, or a detectable moiety, can vary as desired by the practitioner. If the element is present in at least one protein set, then that number can range, for example, from 1 to 10, or up to the total number of protein sets in the standard. The number of protein sets comprising a mixture of labeled and unlabeled proteins can similarly vary.

In some aspects, it can be advantageous to impart different features to different protein sets of the standard. For example, a protein of one set may have a red label, while a protein of a different set may have a blue label. Different colors permit the bands corresponding to these protein sets to be easily identified by eye, allowing a practitioner to gauge the progress of protein migration while the gel is running and 'orient' the gel when handling it. Accordingly, in some embodiments, the label of a protein in one protein set is spectrally distinct from the label of a protein in a different protein set. Such spectral distinction can also apply to fluorescent labels: a diversity of labels in the protein standard allows characterization of a broader range of fluorescent sample proteins that may be run in the gel alongside the standard, because the standard can be detected at more emission wavelengths. By the same reasoning, it can also be advantageous to equip protein sets of the standard with different epitopes or affinity tags, to allow detection of standard and sample proteins with a greater range of binding partners.

Different protein sets of the standard correspond to different molecular weights. For example, one set may comprise proteins of approximately 50 kDa, while another set may comprise proteins of approximately 200 kDa. The weights of proteins within a set may vary, for example due to non-uniform labeling or other sources of molecular heterogeneity as discussed above. However, the differences in weight between proteins within a set are, in some embodiments, much smaller than the differences between proteins from different sets. In some embodiments, protein sets of the standard differ in molecular weight by at least 1, 2, 5, 10, 20, 50, or 100 kDa. In some embodiments, protein sets correspond to molecular weights in the range 10 to 250 kDa.

A protein standard with multiple protein sets usually comprises multiple amino acid sequences. Proteins from two sets usually have different amino acid sequences, although they can also be distinguished from each other by covalent modifications. A further advantage of imparting different detectable features to different protein sets of the standard is that these features can be tailored to the amino acid sequence(s) present in each set. For example, a fluorescent label may be present in only one set because the associated labeling chemistry is only compatible with the amino acid sequence of the protein in this set. Without limiting the universe of amino acid sequences available for use in the protein standard, the proteins of each set may comprise one amino acid sequence or more than one amino acid sequence. The amino acid sequences employed in the standard may be naturally occurring or engineered. Examples of naturally occurring proteins available for use in protein standards may be found in Weber and Osborn, *J. Biol. Chem.* 244, 4406-4412, 1969, and elsewhere.

The stoichiometry of protein labeling and the mixing of labeled and unlabeled proteins, discussed above, have implications for the concentration of protein that must be loaded into an electrophoresis gel to obtain the desired levels of optical signal. In preparing one protein set, reducing the stoichiometry of labeling, or reducing the amount of labeled protein relative to unlabeled protein in a mixture, lowers the average number of labels per protein molecule, all else being equal. Fewer labels per molecule mean that a greater mass of the protein set must be loaded in order to detect the label. This holds true for all kinds of labels contemplated herein; the same logic applies when considering the average number of haloalkylated tryptophan residues, polypeptide moieties, etc., per molecule. Therefore, in some embodiments of the invention, at least one protein set of the standard is loaded (or occurs) in the gel at a concentration of at least 0.1, 0.2, 0.5, 1, 2, 5, or 10 micrograms per lane, or at a concentration in the range 0.1-10, 0.2-10, 0.5-10, 1-10, 2-10, or 5-10 micrograms per lane. In some embodiments, all protein sets of the standard are loaded in the gel at one of these minimum concentrations or ranges of concentrations.

The entire standard is an admixture of multiple protein sets, and so raising the concentration of one protein set also raises the concentration of the entire standard. Therefore, in some embodiments, the protein standard occurs in the gel at a concentration of at least 0.5, 1, 2, 5, 10, 20, 30, or 40 micrograms total protein per lane, or at a concentration in the range 0.5-40, 1-40, 2-40, 5-40, 10-40, 20-40, or 30-40 micrograms per lane. The amount of a protein set needed to obtain the desired level of signal from the gel is a function of not only the composition of the protein set, but also the dimensions of the gel, the sensitivity of the detection apparatus, and other factors.

As used herein, a 'detection modality' refers to a method or apparatus for detecting standard or sample proteins in an electrophoresis gel. The simplest such modality is visualization: a protein covalently linked to a colored label, if at sufficient concentration, can be observed through a transparent (e.g. glass) gel rig while the gel is running, on a light box after the gel has been removed from the rig, or at other convenient times. Ambient or white light may be used to illuminate the gel and perform such visualization. As discussed above, a UV transilluminator can be used for the detection of haloalkylated tryptophan residues in a gel after running Such an apparatus also finds use in detecting nucleic acids in electrophoresis gels, for example in conjunction with ethidium bromide and SYBR dyes. For detection of proteins linked to fluorescent labels, the gel may be illuminated with a laser, LED, or other appropriate narrow-spectrum light source to provide excitation, and fluorescently re-emitted light may be detected using standard filters and other optics, at wavelengths appropriate for the particular labels. In standard three-channel fluorescence set-ups, which may be employed here, excitation occurs in the red, green, and blue portions of the visible spectrum (~630, 530, and 490 nm, respectively), and emission is monitored at longer wavelengths. Instruments for detecting fluorescence in electrophoresis gels are available commercially. Any of the foregoing light sources may be coupled to a camera and computer for image acquisition, processing (e.g. quantitation), and storage.

Modalities related to the detection of proteins on blots, such as after electroblotting, are known. A blot may be placed in proximity to a piece of photographic film to capture chemiluminescence or radioactivity arising from porphyrins, antibodies, etc., as discussed above. After sufficient exposure time, the film may be developed using standard methods. Alternatively, the blot may be imaged using a CCD camera. For detection of fluorescent labels or haloalkylated tryptophan residues, an appropriate excitation light source may be coupled to the camera as described above.

EXAMPLES

Example 1

Detection of Protein Standards Using Four Modalities

A 4-20% TGX Stain-Free™ polyacrylamide gel (Bio-Rad) was loaded with three protein standards, each in a separate lane, and run. The three standards had the following compositions:

Standard 1: Precision Plus Unstained Standard, Bio-Rad Cat. No. 161-0363

Standard 2: an admixture of (a) Precision Plus All-Blue Standard, Bio-Rad Cat. No. 161-0373, (b) 25, 50, and 75 kDa proteins each stained with a fluorescent, pink-colored dye, (c) fluorescently stained 37 kDa protein, and (d) 10 kDa protein stained with a fluorescent, yellow-colored dye.

Standard 3: 25 kDa protein costained with QXL610 and Bodipy TMR-X.

Figure 1:
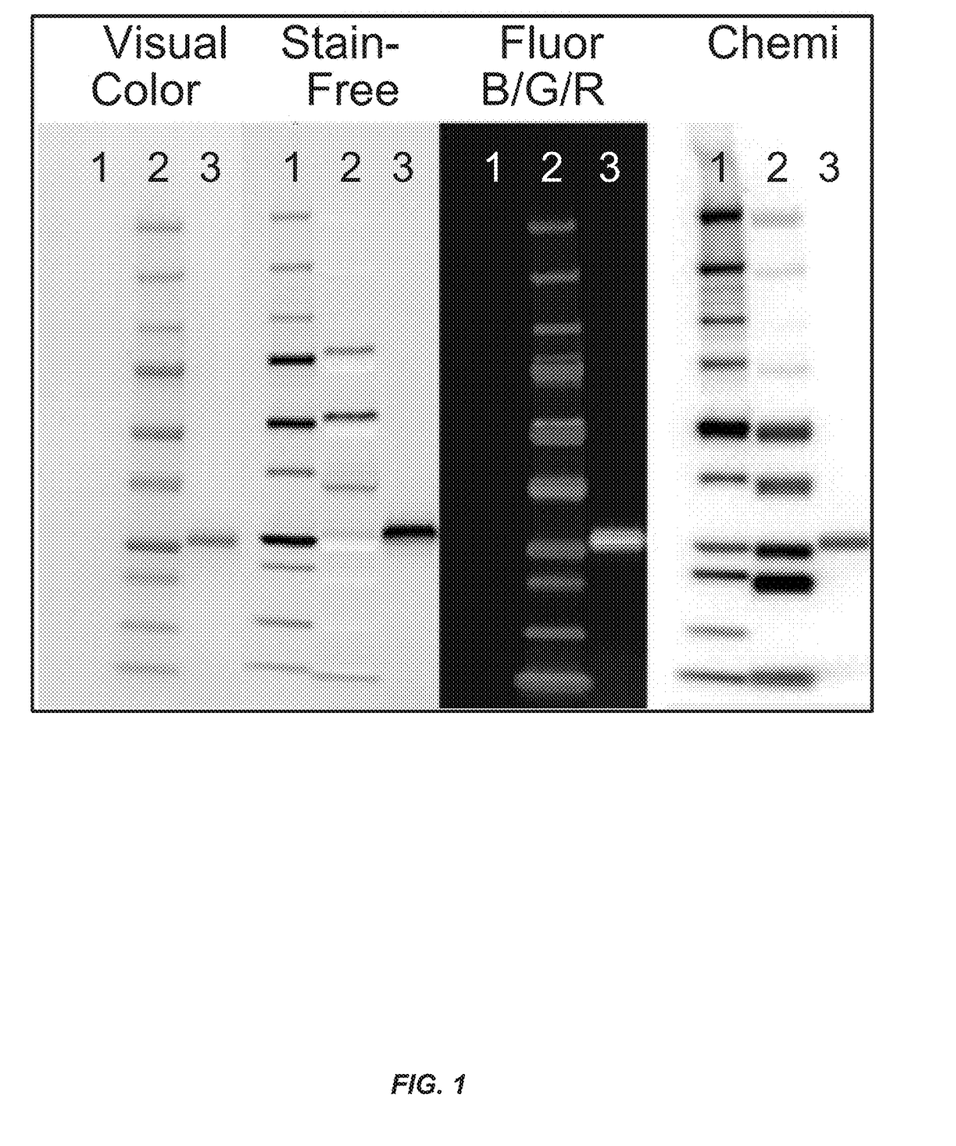
FIG. 1 shows detection of three protein standards in a gel using four detection modalities, as discussed in Example 1.

After the gel was run, proteins in the gel were detected using four modalities (FIG. 1). First, colored proteins were directly visualized under ambient light. Second, proteins having free tryptophan residues were visualized by exposing the gel to UV light, thereby covalently linking such residues to haloalkanes in the gel, and detecting fluorescent emission from haloalkylated tryptophan at ~450 nm. Third, fluorescently labeled proteins were detected using three-channel fluorescence, by exposing the gel to visible light at blue, green, and red wavelengths, and detecting re-emitted light at longer wavelengths. Fourth, proteins containing a Strep-tag were visualized using chemiluminescence, by electroblotting proteins from the gel onto PVDF membrane, incubating the membrane with Strep-Tactin-HRP, and detecting HRP-catalyzed oxidation of luminol.

The lane of the gel containing Standard 1 showed no visible color or fluorescence. However, 10 bands appeared in this lane when the gel was exposed to UV light for haloalkylation and detection of tryptophan residues. The 10 bands appeared in roughly the same pattern when proteins were visualized on the membrane using chemiluminescence.

Standard 2 was detected using all four modalities. Proteins of the standard, ranging in molecular weight from 10 to 250 kDa, appeared blue when the gel was visualized directly, except for the 37 kDa protein, which appeared as a green band due to costaining with blue and yellow dyes. When the gel was exposed to UV light, bands appeared in the Standard 2 lane at approximately 10, 25, 37, 50, and 75 kDa. Using three-channel fluorescence, 10 red bands appeared on the gel due to one common fluorescent dye. The 10, 50, and 75 kDa bands were bifurcated, with green fluorescence appearing above red fluorescence at 50 and 75 kDa, and red fluorescence appearing above blue fluorescence at 10 kDa. The green and blue fluorescence in these bands was due to proteins stained with pink- and yellow-colored fluorescent dyes, respectively. On the blotting membrane, strong chemiluminescent bands appeared at 10, 20, 25, 37, and 50 kDa. Therefore, the 10, 25, 37, and 50 kDa proteins were detected with all four modalities.

Standard 3 gave rise to one band, seen with all detection modalities. The colored band appeared purple and the fluorescent band appeared bifurcated, with green fluorescence appearing above red fluorescence. The band also appeared in the Standard 3 lane when the gel was illuminated with UV light, and when proteins from the gel were detected using chemiluminescence following electroblotting. The band occurred at roughly the same location, corresponding to a molecular weight of approximately 25 kDa, when detected with the four modalities.

Example 2

Detection of Protein Standards Using Three Modalities

A 4-20% TGX Stain-Free™ polyacrylamide gel (Bio-Rad) was loaded with five protein standards, each in a separate lane, and run. The standards had the compositions shown in Table 1 below. The standards in lanes 3, 4, and 5 had common components, as well as additional components specific to each standard.

Figure 2A:
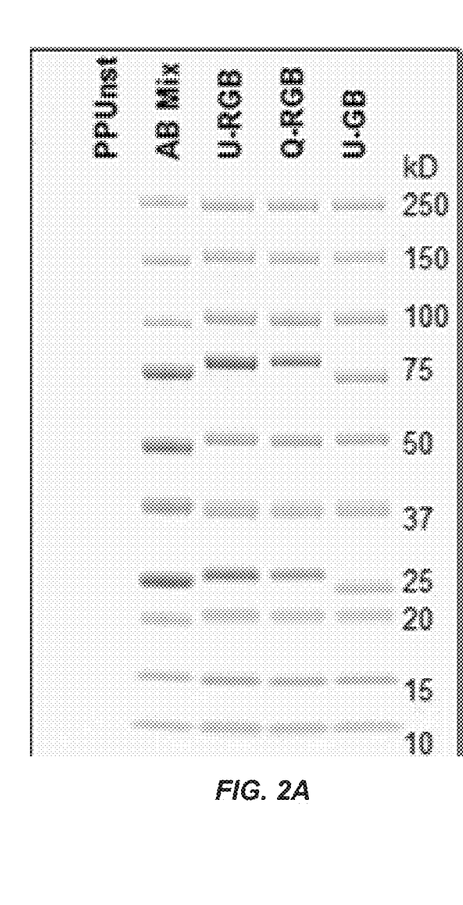
FIG. 2A shows a gel containing the protein standards illuminated with ambient light.
Figure 2B:
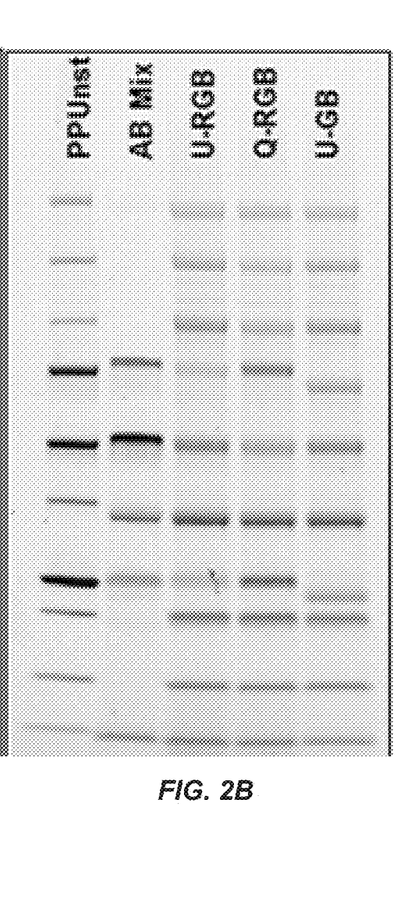
FIG. 2B shows the gel illuminated with UV light.
Figure 2C:
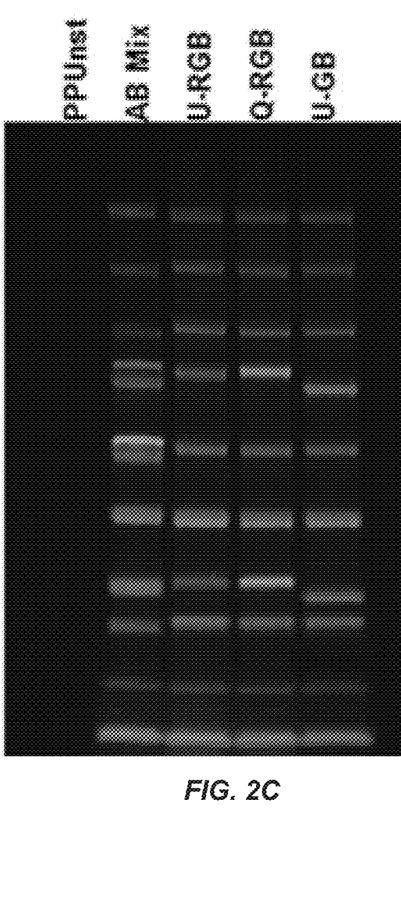
FIG. 2C is a merged image resulting from separate exposures of the gel to red, green, and blue wavelength light.

After the gel was run, proteins in the gel were detected using three modalities. The gel was exposed to ambient light to detect colored labels (FIG. 2A); UV light to detect fluorescent haloalkylated tryptophan residues (FIG. 2B); and visible light (at red, green, and blue wavelengths) to detect fluorescent labels (FIG. 2C). Detection using these modalities was performed as described in Example 1.

TABLE 1

Names and compositions of standards in Example 2.

| Lane | Name of standard | Composition of standard |
|---|---|---|
| 1 | PPUnst | Precision Plus Unstained Standard, Bio-Rad Cat. No. 161-0363 |
| 2 | AB Mix | admixture of (a) Precision Plus All-Blue Standard, Bio-Rad Cat. No. 161-0373, (b) 25, 50, and 75 kDa proteins each stained with a fluorescent, pink-colored dye, (c) 37 kDa protein costained with fluorescent, blue- and yellow-colored dyes, and (d) 10 kDa protein stained with a fluorescent, yellow-colored dye. |

TABLE 1-continued

Names and compositions of standards in Example 2.

| | | Common | Additional |
|---|---|---|---|
| 3 | U-RGB | Uniblue A-stained 10 kDa protein; NBD-X-stained 10 kDa protein; Uniblue A-stained 15 kDa protein; 15 kDa unstained protein; Uniblue A/DEAC-costained 37 kDa protein; Uniblue A-stained 250 kDa protein; 250 kDa unstained protein | Uniblue A/Dansyl X-costained 20, 50, 100, and 150 kDa proteins; Uniblue A/Bodipy TMR-X-costained 25 and 75 kDa proteins |
| 4 | Q-RGB | | QXL610/Dansyl X-costained 20, 50, 100, and 150 kDa proteins; QXL610/Bodipy TMR-X-costained 25 and 75 kDa proteins |
| 5 | U-GB | | Uniblue A/Dansyl X-costained 20, 50, 100, and 150 kDa proteins; Uniblue A/DEAC-costained 25 and 75 kDa proteins |

The standards all contained proteins having molecular weights of approximately 10, 15, 20, 25, 37, 50, 75, 100, 150, and 250 kDa. With exceptions, 10 bands (one at each of these weights) appeared in each lane for each detection modality; with exceptions, corresponding bands from the different lanes had the same mobility on the gel. The exceptions are discussed below.

The Precision Plus Unstained Standard (PPUnst, which was the same as Standard 1 in Example 1) did not appear at all when the gel was visualized under ambient light or using three-channel fluorescence. This is because none of the proteins in this standard comprised a colored or fluorescent label. The other standards could be detected using all three modalities.

For the AB Mix standard (which was the same as Standard 2 in Example 1), bands appeared at 10, 25, 37, 50, and 75 kDa when the gel was exposed to UV light. The absence of bands at other molecular weights suggests that many of the proteins of the Precision Plus All-Blue Standard did not have free tryptophan residues available for haloalkylation, or were dye-labeled in such a way that UV fluorescence from haloalkylated tryptophan residues was suppressed. When detecting the AB Mix standard with three-channel fluorescence, the 50 and 75 kDa bands appeared bifurcated, as they did in Example 1, and so did the 25 kDa band. For each of these bands, green fluorescence appeared above red fluorescence. These pink fluorescently stained proteins appear to migrate with higher molecular weights than corresponding proteins from the All-Blue Standard with which they were mixed.

Most proteins from the standards in lanes 3-5 appeared blue when illuminated with ambient light, because most of the proteins in these lanes were labeled with Uniblue A or QXL610. However, proteins costained with Uniblue A and DEAC, including the 37 kDa protein present in all three of these standards, and the 25 and 75 kDa proteins in the U-GB standard, appeared green. The 25 and 75 kDa proteins in the U-RGB and Q-RGB standards, costained with Uniblue A or QXL610 and Bodipy TMR-X, appeared purple. None of the colored bands for these costained proteins appeared bifurcated, indicating that the typical protein molecule in these bands was attached to both costaining dyes.

A merged fluorescent image of the gel (FIG. 2C) was prepared by illuminating the gel with red, green, and blue light in separate exposures, detecting fluorescently re-emitted light from each exposure to obtain an image, and overlaying the three images. Most bands in lanes 3-5 of the merged image appeared red, again due to the prevalence of the Uniblue A and QXL610 dyes. Several bands in the gel appeared bifurcated, including the 25, 50, and 75 kDa bands in the AB Mix standard, discussed above. The 10 kDa bands in lanes 3-5 also appeared bifurcated, with red fluorescence appearing above blue fluorescence, because the standards in these lanes all contained a mixture of Uniblue A and NBD-X-stained 10 kDa proteins. However, the 25 and 75 kDa proteins in the U-RGB and Q-RGB standards did not give rise to bifurcated bands, with red and green fluorescence co-localizing. The lack of bifurcation, also seen when visualizing these proteins under ambient light, and the fact that these proteins generally migrated more slowly than the 25 and 75 kDa proteins from the other standards (as seen with all three detection modalities), is consistent with the particular pink dye being used in the staining.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A protein standard for gel electrophoresis, the standard comprising multiple protein sets, each set corresponding to a different gel band, wherein at least one set comprises a mixture of unlabeled and labeled proteins, said unlabeled protein comprising a tryptophan residue, and said labeled protein comprising a label that is spectrally distinct from haloalkylated tryptophan.

2. The protein standard of claim 1, wherein the label is an amino acid residue covalently linked to a dye.

3. The protein standard of claim 1, wherein 2, 3, 4, 5, 6, 7, 8, 9, 10, 11 or 12 protein sets of the standard comprise a protein comprising such a label.

4. The protein standard of claim 3, wherein the label of a protein of a first protein set is spectrally distinct from the label of a protein of a second protein set.

5. The protein standard of claim 1, wherein all protein sets of the standard comprise a protein comprising such a label.

6. The protein standard of claim 1, wherein the label is stable in the presence of reducing agents.

7. The protein standard of claim 1, wherein the labeled protein of the at least one set further comprises a detectable moiety.

8. The protein standard of claim 7, wherein the moiety is a porphyrin.

9. The protein standard of claim 7, wherein the moiety is a polypeptide.

10. The protein standard of claim 9, wherein the polypeptide is a recognition sequence.

11. The protein standard of claim 1, comprising multiple protein sets, each set corresponding to a different gel band, wherein at least one set comprises a protein comprising the amino acid sequence WTHPQFER (SEQ ID NO: 1), AWRHPQFGG (SEQ ID NO: 2), or WSHPQFEK (SEQ ID NO: 3).

12. The protein standard of claim 11, wherein the protein of the at least one set further comprises a label, said label comprising an amino acid residue covalently linked to a dye.

13. A method of detecting a protein standard after gel electrophoresis, the method comprising:
   providing an electrophoresis gel comprising the protein standard of claim 1; and,
   optically detecting the standard.

14. The method of claim 13, further comprising illuminating the gel with UV light and detecting the fluorescence of any haloalkylated tryptophan residues in the standard.

15. The method of claim 13, further comprising:
   transferring the labeled protein from the gel to a blotting membrane; and,
   detecting the labeled protein on the membrane.

16. The method of claim 15, wherein detection of the labeled protein on the membrane comprises:
   providing a binding partner specific for the label or moiety of the labeled protein;

incubating the membrane with the binding partner; and,
detecting the interaction of the binding partner with the labeled protein on the membrane.

17. A kit for detecting a protein standard in a gel, the kit comprising:
the protein standard of claim 1; and,
a haloalkane.

18. The kit of claim 17, wherein a labeled protein of the standard comprises a moiety detectable on a blotting membrane, and the kit further comprises a binding partner specific for said moiety for use in such detection.

* * * * *